United States Patent
Le Maner

(10) Patent No.: US 10,668,228 B2
(45) Date of Patent: Jun. 2, 2020

(54) LATERALLY-ACTUATED FLUID PRODUCT DISPENSING DEVICE

(75) Inventor: Francois Le Maner, La Vallee Montaure (FR)

(73) Assignee: APTAR FRANCE SAS, Le Neubourg (FR)

( * ) Notice: Subject to any disclaimer, the term of this patent is extended or adjusted under 35 U.S.C. 154(b) by 295 days.

(21) Appl. No.: 14/005,131

(22) PCT Filed: Mar. 19, 2012

(86) PCT No.: PCT/FR2012/050569
§ 371 (c)(1),
(2), (4) Date: Sep. 13, 2013

(87) PCT Pub. No.: WO2012/127163
PCT Pub. Date: Sep. 27, 2012

(65) Prior Publication Data
US 2014/0000587 A1     Jan. 2, 2014

(30) Foreign Application Priority Data

Mar. 21, 2011   (FR) ...................................... 11 52304

(51) Int. Cl.
*A61M 11/02*     (2006.01)
*B05B 11/00*     (2006.01)
(Continued)

(52) U.S. Cl.
CPC .......... *A61M 11/02* (2013.01); *A61M 15/009* (2013.01); *A61M 15/0081* (2014.02);
(Continued)

(58) Field of Classification Search
CPC .................................................. A61M 11/02
(Continued)

(56) References Cited

U.S. PATENT DOCUMENTS

| 2005/0224525 A1* | 10/2005 | Davies .................. A61M 15/08 222/402.15 |
| 2011/0062186 A1* | 3/2011 | Julia .................... B05B 11/0059 222/153.04 |
| 2011/0062188 A1* | 3/2011 | Lemaner ............. A61M 15/009 222/162 |

FOREIGN PATENT DOCUMENTS

| EP | 1 974 828 A2 | 10/2008 |
| FR | 2 812 826 A1 | 2/2002 |

(Continued)

OTHER PUBLICATIONS

English translation of the International Preliminary Report on Patentability for PCT/FR2012/050569.
(Continued)

*Primary Examiner* — Timothy A Stanis
*Assistant Examiner* — Victoria Murphy
(74) *Attorney, Agent, or Firm* — Sughrue Mion, PLLC

(57) ABSTRACT

A fluid dispenser device having a body (10), a reservoir (20), a dispenser head (100) and a dispenser member (30) mounted on the reservoir by a fastener ring (60). Also provided is a lateral actuator system (40) including an actuator element (41) movable between a rest position and an actuated position. The body (10) includes a guide surface (50) that is stationary relative to the head and substantially parallel to the central axis of the dispenser member (30). The actuator element (41) co-operates with the guide surface (50). The guide surface (50) includes a resistance element (55) that modifies the co-operation between the actuator element (41) and the guide surface (50). In order to be passed over, the resistance element (55) require the user to act on the lateral actuator system (40) with an actuation force that is different.

13 Claims, 7 Drawing Sheets

(51) Int. Cl.
*A61M 15/08* (2006.01)
*B65D 83/22* (2006.01)
*B65D 83/38* (2006.01)
*A61M 15/00* (2006.01)

(52) U.S. Cl.
CPC ......... *A61M 15/08* (2013.01); *B05B 11/0038* (2018.08); *B05B 11/3056* (2013.01); *B05B 11/3059* (2013.01); *B65D 83/226* (2013.01); *B65D 83/386* (2013.01); *B05B 11/3019* (2013.01)

(58) Field of Classification Search
USPC .................................................. 128/200.14
See application file for complete search history.

(56) References Cited

FOREIGN PATENT DOCUMENTS

| | | |
|---|---|---|
| FR | 2 929 252 A1 | 10/2009 |
| WO | 2005/044354 A1 | 5/2005 |
| WO | 2005/075105 A1 | 8/2005 |
| WO | 2006/109021 A1 | 10/2006 |
| WO | 2009/068877 A1 | 6/2009 |
| WO | 2009/153513 A1 | 12/2009 |

OTHER PUBLICATIONS

International Search Report for PCT/FR2012/050569 dated Jun. 13, 2012.

\* cited by examiner

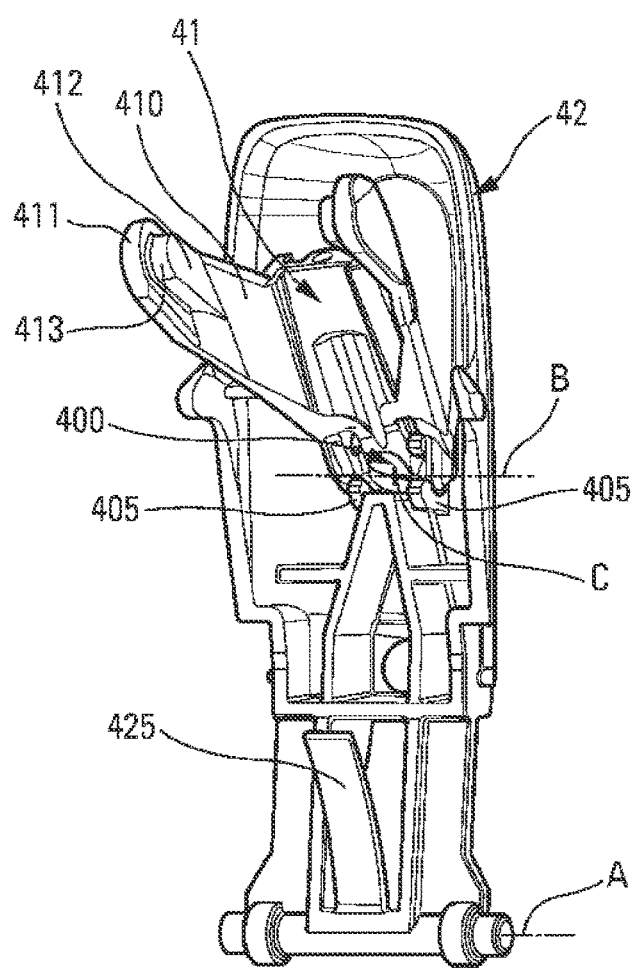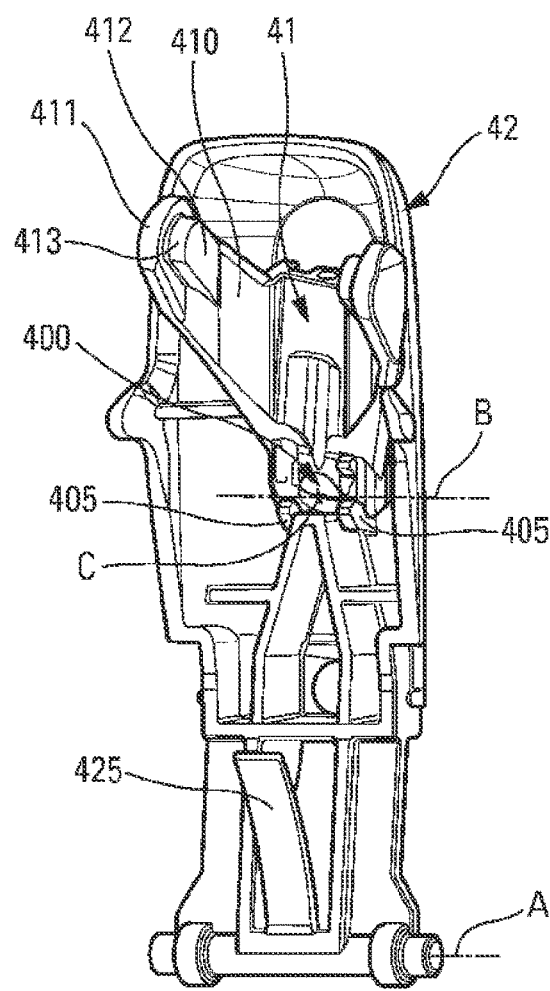
Fig. 6                    Fig. 7

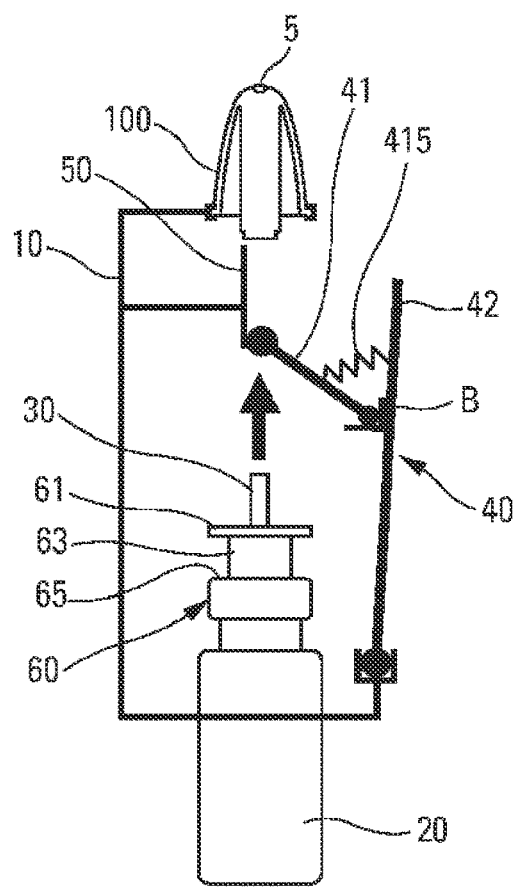
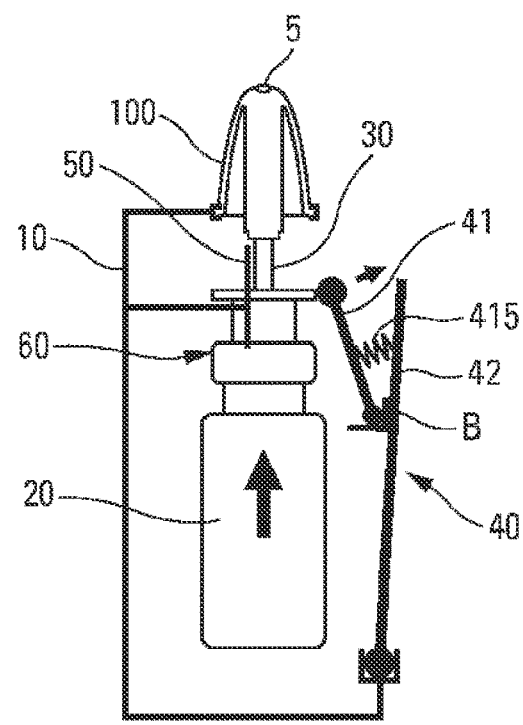
Fig. 10
Fig. 11
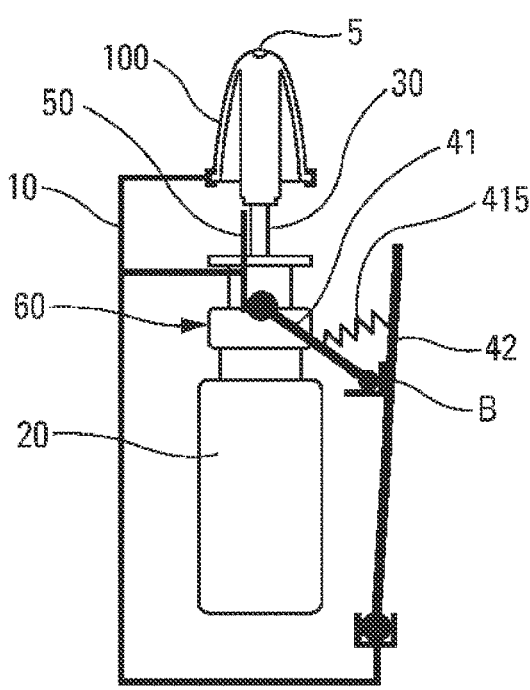
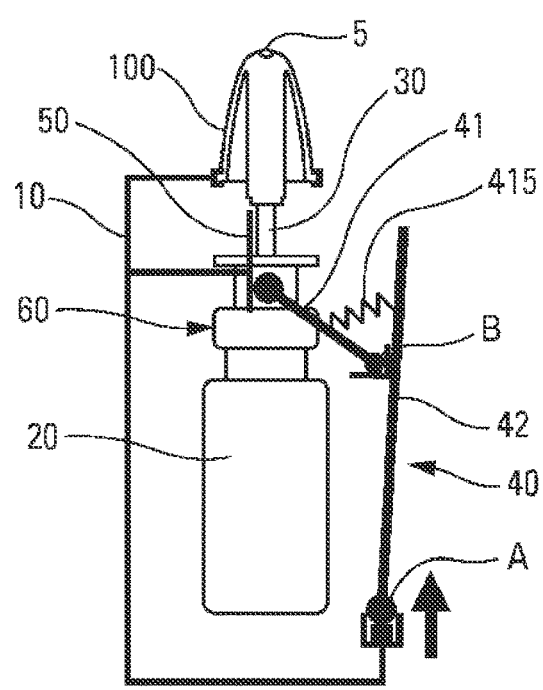
Fig. 12
Fig. 13

LATERALLY-ACTUATED FLUID PRODUCT DISPENSING DEVICE

CROSS REFERENCE TO RELATED APPLICATIONS

This application is a National Stage of International Application No. PCT/FR2012/050569 filed Mar. 19, 2012, claiming priority based on French Patent Application No. 11 52304 filed Mar. 21, 2011, the contents of all of which are incorporated herein by reference in their entirety.

The present invention relates to a laterally actuated fluid dispenser device, and more particularly to a nasal-spray device for a pharmaceutical.

Fluid dispenser devices are well known in the state of the art. They generally include a reservoir containing the fluid, on which reservoir there is assembled a dispenser member, e.g. a pump or a valve, that is generally actuated by means of a dispenser head for selectively dispensing the fluid contained inside said reservoir. The dispenser head includes a dispenser orifice through which the fluid is sprayed, e.g. into the user's nose for a nasal-spray device. Numerous devices of this type are actuated manually by the user by moving the reservoir and the dispenser head axially against each other, thereby actuating the dispenser member. However, this type of device presents drawbacks, in particular when the device is of the nasal-spray type, since the axial force exerted by the user in order to actuate the device leads to a risk of the dispenser head moving inside the user's nostril, with risks of injury and/or of the fluid not being dispensed completely or properly on actuation. In order to remedy this problem, lateral actuator devices have been proposed, generally including a lever that is pivotally mounted on a body and that has an inner portion that is adapted to co-operate with one of the dispenser head and the reservoir so as to move said element against the other, and thus actuate the dispenser member. However, such lateral actuator devices present a certain number of problems. Thus, they generally induce radial stresses during actuation, which stresses may also have negative influences on the spraying of the composition into the user's nostril. They may present problems of reliability during actuation, with, in some circumstances, risks of blockages that might prevent any actuation. Generally, they include movable parts that impose a clearly defined actuation direction, with risks of malfunctioning in the event of actuation in a direction that is a little offset. They potentially generate noise during actuation or when the device is shaken, and this can be perceived negatively by the user. They are often quite difficult to assemble, and assembly is generally possible only after filling with the fluid that is to be dispensed, and this imposes complex assembly lines for a manufacturer of the active substances who is generally different from the manufacturer of the lateral actuator device. Documents WO 2005/075105 and WO 2009/153513 describe prior-art devices.

An object of the present invention is to provide a laterally actuated fluid dispenser device that does not have the above-mentioned drawbacks.

Another object of the present invention is to provide a laterally actuated fluid dispenser device, in particular a nasal spray, that guarantees safe and reliable actuation of the device on each actuation, without risk of injury to the user.

More particularly, an object of the present invention is to provide a fluid dispenser device that is simple and inexpensive to manufacture and to assemble.

The present invention thus provides a fluid dispenser device comprising a body, a reservoir, a dispenser head incorporating a dispenser orifice, and a dispenser member, such as a pump or a valve, that is mounted on said reservoir by means of a fastener ring, said dispenser member comprising a dispenser-member body and a movable member that moves axially in said dispenser-member body while said dispenser member is being actuated, said device further comprising a lateral actuator system that is secured to said body, said system including an actuator element that is movable, substantially transversally to the direction of movement of said movable member, between a rest position in which said dispenser member is not actuated, and an actuated position in which said dispenser member is actuated, said body including at least one guide surface for guiding said actuator element, said at least one guide surface being stationary relative to said dispenser head and substantially parallel to the movement axis of the movable member in the dispenser-member body while said dispenser member is being actuated, said actuator element including at least one end edge that is preferably rounded and that co-operates with said at least one guide surface, said at least one guide surface including resistance means that modify the co-operation between said actuator element and said guide surface, in order to be passed over, said resistance means require the user to act on said lateral actuator system with an actuation force that is different.

Advantageously, said resistance means comprise a profile, such as a shoulder or a projection, that is formed on said guide surface, said actuator element needing to pass over said profile in order to achieve actuation.

Advantageously, said profile co-operates with said actuator element from the beginning of the actuation stroke.

In a variant, said profile co-operates with said actuator element after a portion of the actuation stroke.

Advantageously, said resistance means include locally modifying the surface state of said guide surface for locally modifying friction between the actuator element and the guide surface.

Advantageously, said lateral actuator system includes a presser element that is mounted on the body to pivot about an axis A, said actuator element being mounted on said presser element to pivot about an axis B.

Advantageously, said actuator element includes a resilient element, such as a resilient blade, that co-operates with said presser element so as to urge said actuator element away from said presser element and into contact with said guide surface.

Advantageously, said actuator element of the lateral actuator system co-operates directly with said fastener ring during actuation.

These characteristics and advantages and others of the present invention appear more clearly from the following detailed description of several embodiments and variants thereof, given by way of non-limiting example, and with reference to the accompanying drawings, and in which:

FIGS. 6 and 7 are diagrammatic perspective views of details of an advantageous embodiment, shown respectively in two different positions;

FIGS. 10 to 13 show diagrams showing four successive stages in the assembly of an advantageous embodiment.

Figure 1:
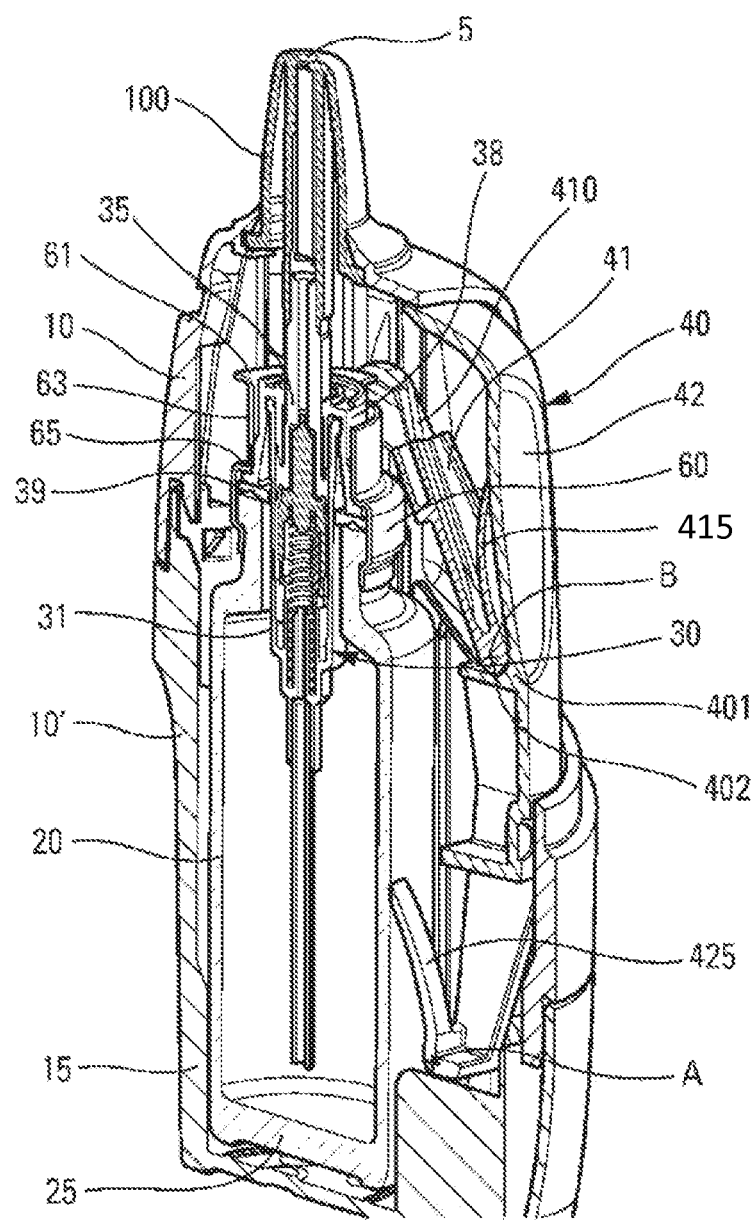
FIG. 1 is a diagrammatic perspective view in section of a device in an advantageous embodiment.
Figure 2:
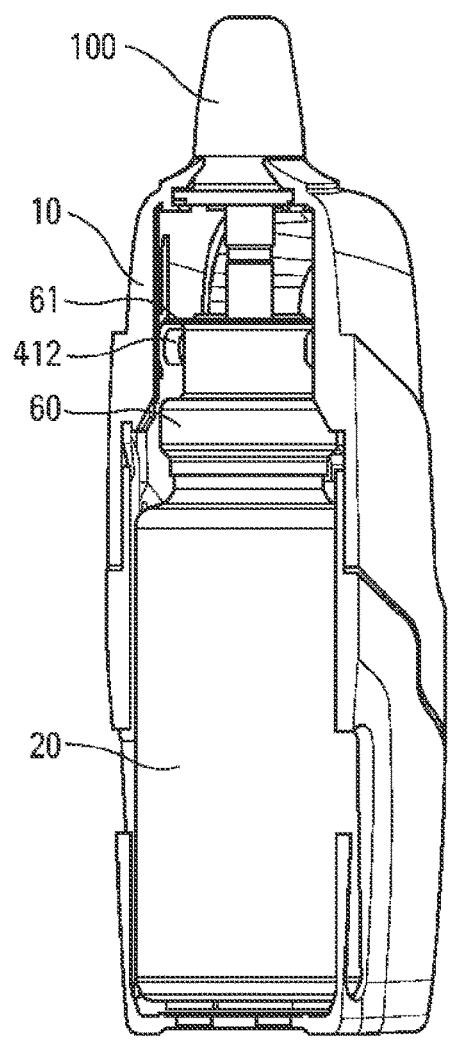
FIGS. 2 and 3 are diagrammatic views of a device in an advantageous embodiment, shown in section respectively in two different section planes.
Figure 3:
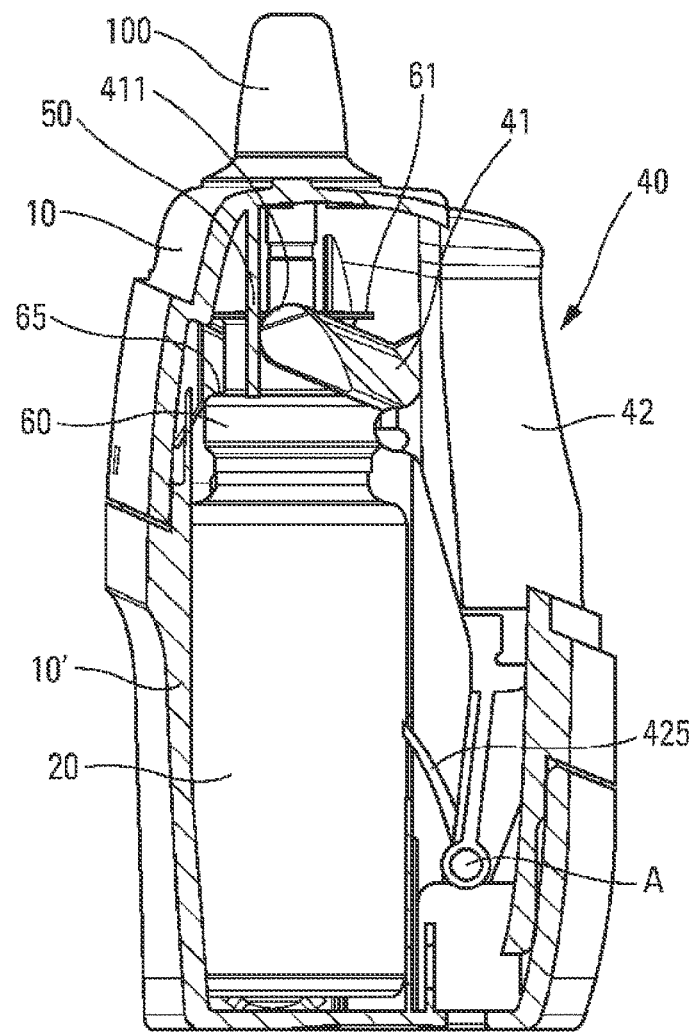

With reference to FIGS. 1 to 3, which show a first advantageous embodiment, the fluid dispenser device includes a body 10 in which there is assembled a reservoir 20 that contains fluid, in particular a pharmaceutical, for spaying into the user's nose. A dispenser member 30, such as a pump or a valve, is assembled on said reservoir 20 by means of a fastener ring 60 that may be crimpable, snap-fastenable, or screw fastenable. The fastener ring 60 may be made of metal, e.g. aluminum, or of plastics material. In a variant, it could also be made of two materials, with one portion made of plastics material and one portion made of metal, typically by overmolding. The dispenser member comprises a dispenser-member body 31, such as a pump body or a valve body, and a movable member 35, such as a piston rod or a valve member, that is mounted to slide axially in said dispenser-member body. In conventional manner, the movable member 35 is driven into the dispenser-member body 31, so as to actuate said dispenser member 30. This is shown diagrammatically in FIG. 1, with the movable member 35, which in this embodiment is a pump piston, in its rest position in a pump body 31. Advantageously, a dispenser head 100 is assembled on said dispenser member 30, said dispenser head 100 incorporating a dispenser orifice 5 through which the fluid is dispensed. In the embodiments shown, the head 100 is secured to the body 10 of the device or is fastened thereto. The head 100 may also be made integrally with said body. The body 10 may be made as a single piece, or it may advantageously comprise a top portion that is associated with the dispenser head 100, and a bottom portion 10' that comes to be fastened to the top portion while the device is being assembled. This is shown in the embodiments in the drawings. In the description below, reference is made to the body 10, with it being understood that this encompasses both of the above-mentioned variants.

The device includes a lateral actuator system 40 that is secured to the body 10 and that is adapted to co-operate with the fastener ring 60 that fastens the dispenser member 30 on the reservoir 20. The lateral actuator system 40 includes an actuator element 41 that is mounted to move inside a presser element 42, in substantially pivoting manner about an axis B. The presser element 42 itself is mounted on the body 10 to pivot about an axis A, substantially parallel to said axis B. The user presses on the presser element 42, preferably via an appropriate presser zone so as to cause the presser element 42 to pivot relative to the body 10, about the axis A. The pivoting of the presser element 42 causes the actuator element 41 to pivot relative to said presser element 42, about the axis B, and thus causes the dispenser member 30 to be actuated. The actuator element 41 is thus movable in a direction that is substantially transverse to the direction in which the movable member 35 of the dispenser member is movable. As can be seen in FIGS. 1, 4, 5, and 8 to 13 in particular, the actuator element 41 advantageously includes a resilient element 415, such as a resilient blade, that bears against the inside of the presser element 42 so as to urge said actuator element 41 resiliently away from said presser element 42. The resilient element could be provided in some other way, e.g. in the form of any spring. The resilient element guarantees that the actuator element 41 is always urged into contact with a guide surface 50, as explained below. It also enables assembly to be safe and reliable, as described below.

In an advantageous aspect, the actuator element 41 co-operates with the presser element 42 via an annular linear connection piece 400, designated below by a multi-directional ball joint. The ball joint not only enables said actuator element 41 to pivot about the axis B, but also enables relative movement between said actuator element 41 and said presser element 42 in other directions, in particular about a pivot axis C that is substantially perpendicular to said axis B. It also enables a certain amount of movement in translation in the direction of axis B. The ball joint is shown in particular in FIGS. 6 and 7. This structure guarantees perfect positioning of the actuator element 41, compensating and/or accommodating manufacturing tolerances of the plastic parts. The ball joint also makes it possible to compensate for poor actuation of the presser element 42 by the user, typically actuation is an offset actuation. This guarantees that the dispenser member 30 is actuated correctly in all circumstances, and thus increases the reliability of the device.

Figure 8:
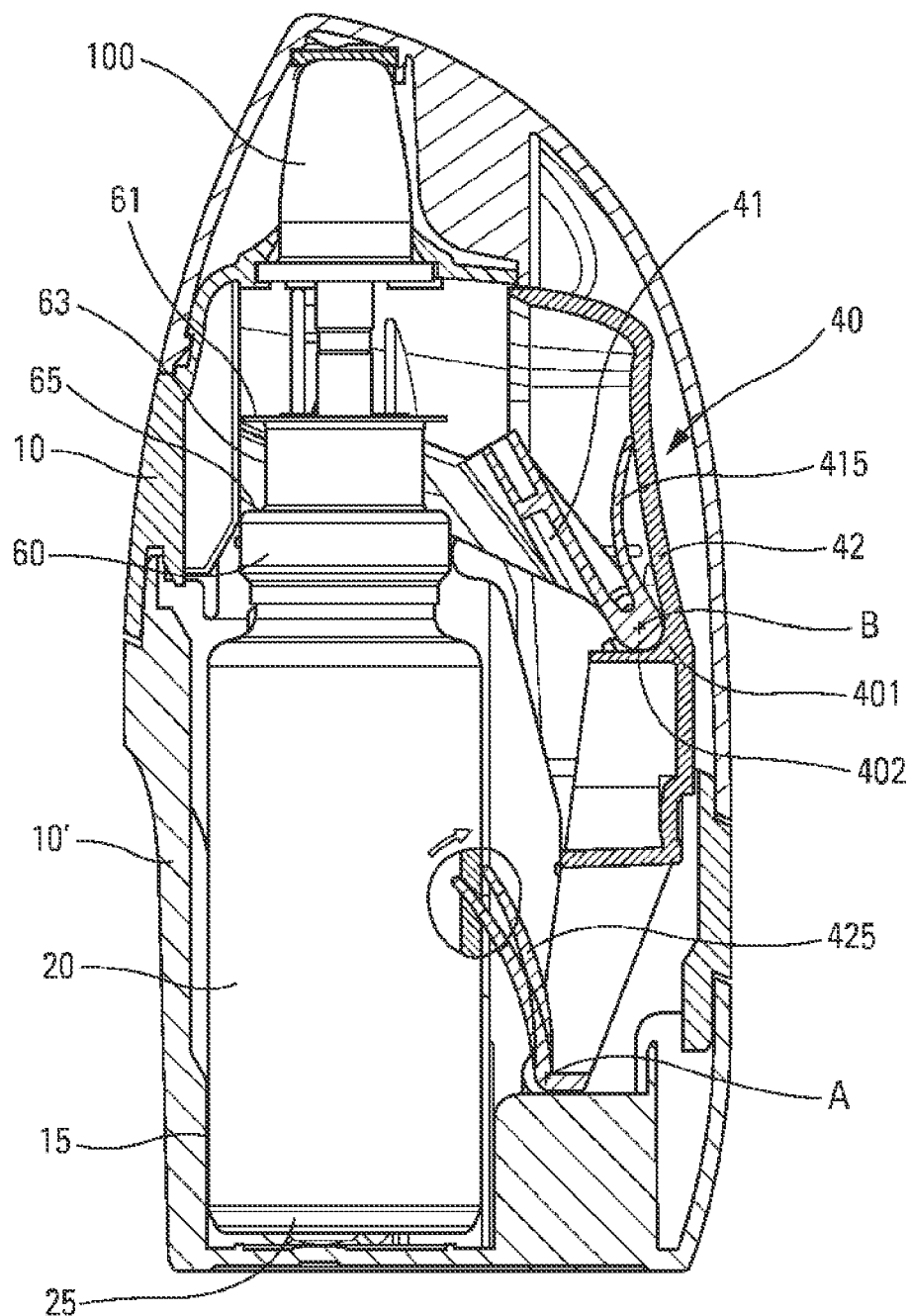
FIG. 8 is a diagrammatic section view of a device in an advantageous embodiment.

Advantageously, said multi-directional ball joint 400 may include a hollow housing 401, as can be seen in FIGS. 1 and 8 in particular, that is rounded at least in part and that is formed on said presser element 42. The actuator element 41 thus includes a complementary profile 402 that co-operates with said hollow housing 401, enabling said actuator element 41 to move on said presser element 42 in at least two different directions, typically at least about axes B and C. A certain amount of movement in translation is also possible along axis B. Naturally, it is possible to envisage relative movement in an infinite number of directions, e.g. if the hollow housing is spherical and if the complementary profile of the actuator element is also spherical and can turn in any direction inside the spherical housing. In an advantageous variant, the hollow housing 401 may have the shape of a rounded groove that extends in the direction of axis B, and the complementary profile formed on the actuator element may include a rounded shape that is suitable for pivoting in said groove and moving in translation along it. In a variant, it may also be envisaged to make the ball joint in inverse manner, with a projecting profile that is rounded in part, e.g. spherical in part, formed on the presser element 42, coming to be positioned in an appropriate hollow housing of the actuator element 41. In this configuration, the hollow housing is formed on the actuator element, and the complementary profile on the presser element. Other variants may also be envisaged.

Preferably, said multi-directional ball joint 400 includes abutment means 405, so as to limit said pivoting about the pivot axis C. As can be seen in FIGS. 6 and 7, the abutment means 405 may comprise two supports that are formed on said presser element 42, projecting from each side of said hollow housing. Each support co-operates with a respective portion of the actuator element 41 so as to define the end positions for pivoting about said pivot axis C, shown in FIGS. 6 and 7 respectively. Advantageously, each of the supports includes a rounded top profile that is adapted to guide said actuator element 41 towards an appropriate position relative to said presser element 42. The actuator element 41 thus also includes rounded portions that co-operate with said rounded profiles of the supports. In particular, this makes it possible to return axis B to being parallel to axis A, in the event of the actuator element 41 pivoting relative to the presser element about a vertical axis in FIGS. 6 and 7, thereby causing one to be offset relative to the other.

Figure 9:
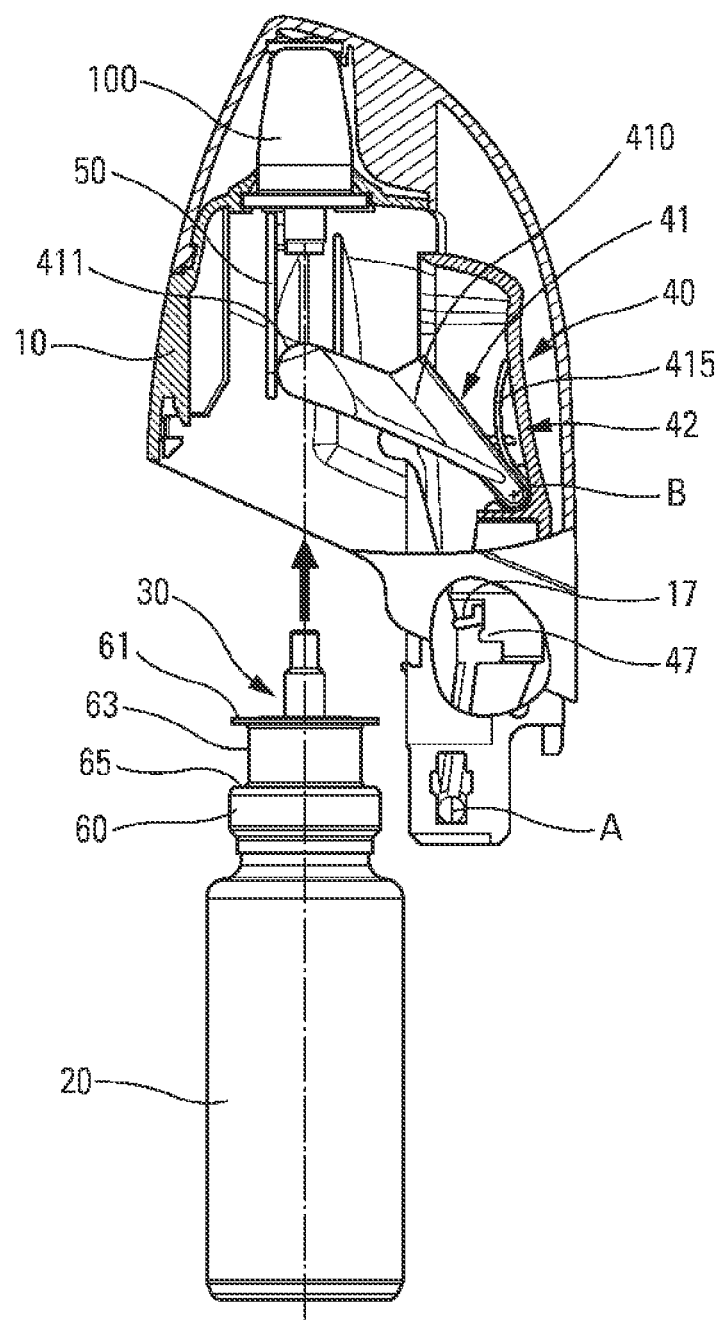
FIG. 9 is a fragmentary and diagrammatic view of a device in an advantageous embodiment, while the device is being assembled.

In another advantageous aspect, the body 10 of the device includes at least one guide surface 50, as can be seen in FIGS. 3 to 5 and 9 to 13 in particular, that serves to guide the actuator element 41 during its actuation stroke, i.e. while it is pivoting, when the user actuates the lateral actuator system 40. As can be seen in FIG. 3 in particular, the guide surface 50 is vertical and axial, i.e. it is substantially parallel to the central axis of the dispenser member, which central axis is the movement axis of the movable member 35 in the dispenser-member body 31 while the dispenser member 30 is being actuated. The guide surface 50 may be plane, as shown in FIG. 3. It is stationary relative to the body 10 and to the dispenser head 100 during actuation. In particular, it may be formed on the body 10, as shown in FIG. 3, or on the head 100, as shown in FIG. 9 in particular. The guide surface 50 thus serves in particular to reduce, and in particular to eliminate, the radial stresses that are exerted by the lateral actuator system 40 while the device is being actuated. In this way, when the user actuates the device, there is no longer any risk of the dispenser head 100 moving sideways in the nostril, with the risk of all or some of the composition being ejected inappropriately. Advantageously, the actuator element 41 includes at least one rounded contact zone 411 for co-operating with the guide surface 50 over the entire actuation stroke. This enables friction against the guide surface to be minimized, so as to minimize the impact of the presence of the guide surface 50 on the resistance of the lateral actuator system to being actuated.

Advantageously, the fastener ring 60 includes a first fastener portion that co-operates with the reservoir 20 so as to fasten said fastener ring 60 on said reservoir 20. In the embodiment shown in FIG. 1, the first portion is crimped on the neck of the reservoir, but a different fastening, e.g. snap-fastening or screw-fastening, may also be envisaged. The fastener ring 60 includes a second portion that co-operates with the dispenser member 30 so as to fasten said dispenser member 30 in said fastener ring 60. By way of example, the second portion may include a shoulder 65 that extends substantially radially inwards and that is adapted to fasten a portion of the dispenser member 30 between said shoulder 65 and the top edge of the reservoir. In the embodiment in FIG. 1, which shows a pump 30 including a piston 35 with a ferrule 38 that defines the rest position of said piston, it is a portion of said ferrule 38 and a neck gasket 39 that are arranged in said second portion of the fastener ring 60. Said ring also includes a third portion that comprises an axial sleeve 63 that is provided at its top end with a top radial flange 61 that extends radially outwards.

In an advantageous aspect, the actuator element 41 optionally co-operates directly with said radial flange 61 of the fastener ring 60 during actuation. In particular, said actuator element 41 advantageously includes at least one flank 410 that extends substantially from the pivot axis B of said actuator element 41 to said guide surface 50. The end edge 411 of said flank 410 is preferably rounded and is adapted to slide over said guide surface 50 during actuation. Each flank 410 further includes a radial projection 412 that extends on one side of said flank in the proximity of its end edge. The radial projection 412 includes a top edge 413 that is preferably rounded and that is adapted to co-operate with the bottom edge of said radial flange 61 of said fastener ring 60, as can be seen in FIG. 1 in particular. It should be observed that in the rest position, it is preferable to provide a small gap between the top edge 413 of the radial projection 412 and the bottom edge of the radial flange 61. The gap may be guaranteed by the resilient blade 415 that urges the actuator element 41 away from the presser element 42. The small gap exists only at the very start of actuation, there is no contact between the actuator element 41 and the radial flange 61, this contact taking place after a small dead stroke at the start of each actuation. This can be seen in FIG. 13 in particular.

The embodiment described in FIGS. 6 and 7 in particular, shows an actuator element 41 with two flanks 410 that are substantially parallel to each other, with the projections 412 facing inwards and thus facing each other. Thus, the two radial projections 412 of the actuator element 41 are arranged outside said axial sleeve 63 of the fastener ring 60, with the top edge 413 of each radial projection 412 in contact with said radial flange 61. Simultaneously, each of the rounded end edges 411 of the two flanks 410 co-operates with a corresponding guide surface 50. This guarantees good robustness, good stability, and reliable operation of the lateral actuator system. This also makes it possible to assemble the actuator element 41 in safe and reliable manner around the fastener ring 60, as described more fully below. Advantageously, said two flanks 410 present a certain amount of springiness that enables them to move apart during assembly and to compensate for certain manufacturing tolerances.

Figure 4:
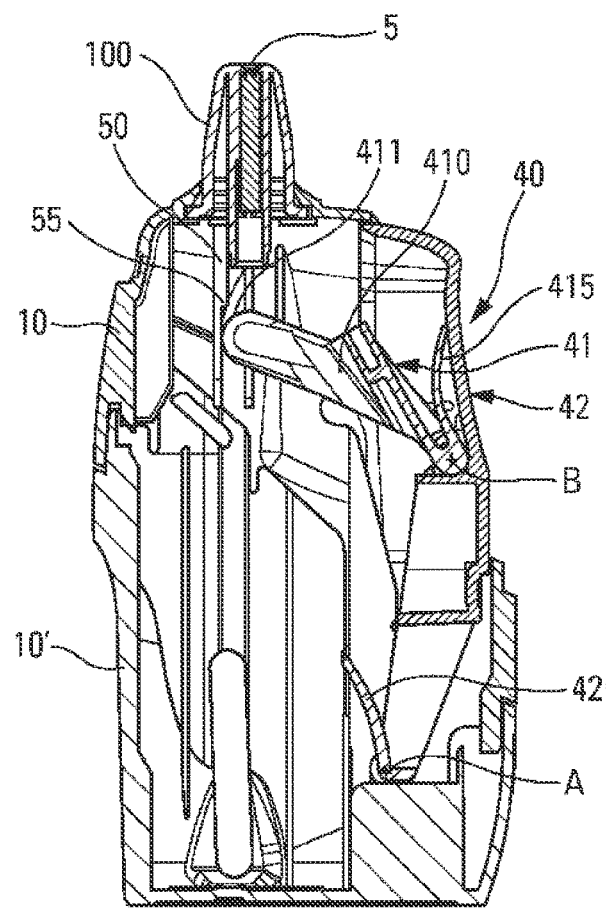
FIGS. 4 and 5 are diagrammatic section views of two advantageous variant embodiments.
Figure 5:
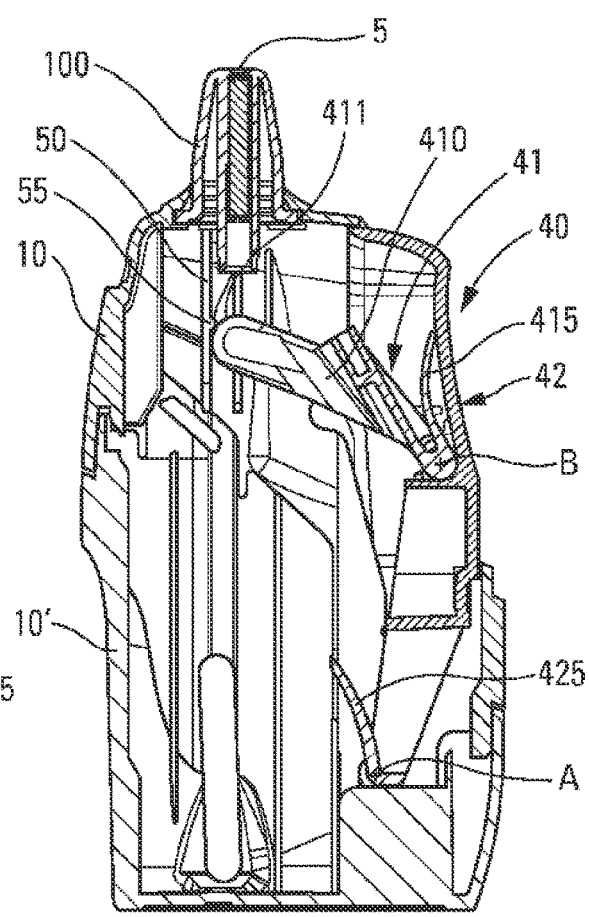

In another advantageous aspect, said at least one guide surface 50 includes resistance means 55 that modify the co-operation between said actuator element 41 and said guide surface 50. Thus, in order to be passed over, said resistance means 55 require the user to act on said actuator element 41 with an actuation force that is different, in particular that is greater. FIGS. 4 and 5 show two variant embodiments in which the guide surface 50 includes a projecting profile 55 on the slide stroke of the actuator element 41. In the embodiment in FIG. 4, the profile includes a shoulder that connects a first guide surface portion to a second guide surface portion. Advantageously, the shoulder slopes, at least a little, it being possible for the slope to be selected as a function of the desired resistance. In the embodiment in FIG. 4, which shows the rest position, it should be observed that said shoulder comes into contact with the rounded end edge 411 of the actuator element after a first portion of the actuation stroke. The user must thus exert a greater force in order to enable said actuator element to pass over said shoulder, and then continue the actuation stroke over the second portion of the guide surface. This guarantees that actuation is complete, and avoids any risk of the dispenser member being poorly actuated. In particular, the shoulder blocks the actuator element until the force exerted by the user is sufficient to pass over the shoulder. The user thus accumulates energy that is suddenly released when the actuator element succeeds in passing over said shoulder. The embodiment in FIG. 5 differs from the embodiment in FIG. 4 in that the guide surface 50 includes a projection that co-operates with the actuator element 41 from the start of its actuation stroke. Thus, in FIG. 5 which also shows the rest position, the actuator element is already in contact with said projection. Thus, right from the start of actuation, the user must exert a force that is sufficient to enable the actuator element to pass over said projection. As in the embodiment in FIG. 4, the user accumulates energy in the hand, which energy is suddenly released after said actuator element has passed over said projection. The actuation stroke is thus complete, guaranteeing correct actuation of the dispenser member.

Other variant embodiments of resistance means are possible, always formed on the guide surface 50. For example, the surface coating of said guide surface may be modified, e.g. so as to increase friction locally and thus constrain the user to exert greater actuation force. Thus, even without a profile or a projection, it is possible to modify the conditions of co-operation between the actuator element and the guide surface.

It is advantageous to form the resistance means on the guide surface, which guide surface is stationary relative to the body and to the head of the device, including during actuation. In particular, it is possible for the force required to pass over the resistance means to be predetermined easily and for it to be reproducible.

Another advantage of the resistance means formed on the guide surface is that they prevent accidental actuation of the device, at least in part. At the start of actuation, or close to the start of actuation, a certain amount of force is required to pass over the resistance means, such that the resistance means provide a certain amount of security against accidental use.

In another advantageous aspect, the reservoir 20 slides in the body 10 during actuation. Thus, the actuator element 41 presses beneath the radial flange 61 of the fastener ring 60, causing the reservoir 20 to move in the body 10. This actuates the dispenser member 30, specifically the pump in the embodiments shown. In order to hold the body 10, in particular during storage or transport, it advantageously includes a sleeve 15 that is adapted to be arranged, at least in part, around a portion of the reservoir 20. As can be seen in FIGS. 1, 3, and 8 in particular, the sleeve 15 advantageously extends around the bottom portion of the reservoir, i.e. around the bottom 25 of said reservoir 20. The sleeve 15 may be annular, but it is preferably formed by a plurality of splines that are spaced apart from one another and that define a hollow annular shape. In order to avoid risking said reservoir blocking during actuation, the sleeve 15 is arranged around the reservoir with a small gap. This structure presents a drawback in that the slightest shaking of the device causes the reservoir to rattle or vibrate inside said sleeve, with associated noises of the rattling type. Firstly, this may be annoying during actuation. Secondly, this may give the user the impression that the device is fragile or is poorly assembled or of poor quality. In order to overcome this drawback, a resilient element 425, such as a resilient blade, may be provided, adapted to co-operate with said reservoir 20 so as to urge it against a side and/or against a spline of said sleeve 15, as shown in FIG. 8. The force of the resilient blade 425 is selected so as to avoid the reservoir vibrating or rattling, but without creating any strong interactions between said reservoir and said sleeve, so as to avoid hindering actuation. Since there is only limited contact between the reservoir and the sleeve, the friction generated by the interaction is negligible. As can be seen in FIG. 8, the resilient blade is preferably formed on the presser element 42 and co-operates with the reservoir 20 outside said sleeve 15. Naturally, other variants can be envisaged. For example, the resilient element could be made in some other way, e.g. separate from the presser element, and it could co-operate with the reservoir within the sleeve.

Thus, the resilient blade 425 that urges the reservoir against the body, associated with the resilient blade 415 that urges the actuator element away from the presser element, guarantee minimum noise generation during actuation, and give the user the overall impression of a device that is of high quality and robust, substantially eliminating the rattling or vibrating noises that are typical of devices provided with lateral actuator systems.

Another advantageous aspect relates to assembling the device. FIGS. 9 to 13 show various assembly steps, FIGS. 10 to 13 being highly diagrammatic so as to simplify understanding of the various steps. As can be seen in FIG. 10, the body 10, the head 100, and the lateral actuator system 40 may be pre-assembled so as to form a first pre-assembled unit. In addition, the dispenser member 30 may be fastened on the reservoir 20 by means of the fastener ring 60, thus forming a second assembled unit. When the second unit is inserted into the first unit, as shown diagrammatically by the arrow in FIG. 10, the actuator element 41 that is urged into contact against the guide surface 50 by the resilient element 415, is moved against the resilient element 415, so as to enable the dispenser member 30 to be assembled in the dispenser head 100, as shown by FIG. 11. In a variant, the head 100 could be assembled on the unit formed by the reservoir and the pump, and then this sub-assembly could be assembled in the unit formed by the body and the lateral actuator system.

Advantageously, the lateral actuator system 40 includes a pre-assembled position in which the presser element 42 is mounted on the body 10 in a pre-assembled position that is axially offset from its final assembled position. FIG. 9 is a diagram showing a blocking portion 17 of the body 10, which blocking portion is adapted to co-operate with a pre-assembly portion 47 of the presser element 42 in the pre-assembled position, so as to block the lateral actuator system 40. When said presser element 42 is moved from its pre-assembled position to its assembled position, the pre-assembly portion 47 of the presser element 42 no longer co-operates with said blocking portion 17 of the body and becomes positioned above said blocking portion as shown in the righthand side of FIG. 9. The pivot axis A of the presser element 42 then becomes operational in its pivot position. Thus, in the position in FIG. 12, the reservoir unit is assembled in the body/head unit, but the presser element 42 is in its pre-assembled position. The lateral actuator system 40 is thus non-operational and any accidental actuation has no effect. In particular, the blocking portion 17 of the body 10 blocks any actuation of the presser element 42 in the pre-assembled position. This structure thus provides, in particular, effective security when transporting the device, even after the reservoir unit has been assembled in the body/head unit. Any actuation of the device is blocked in this position. When assembly is to be made permanent, the presser element 42 is moved axially upwards into the position shown in FIG. 13, and this enables the actuator element 41 to take up its operational position below the radial flange 61 and on the outside of the axial sleeve 63 of the fastener ring 60. The fact that the resilient element 415 resiliently urges the actuator element 41 away from the presser element 42 guarantees safe and reliable assembly as soon as the presser element 42 is moved from its pre-assembled position to its assembled position. Advantageously, the presser element 42 is moved from its pre-assembled position to its assembled position when the bottom portion 10' of the body is assembled on the body 10. Naturally, when the body is made as a single part, other means may be provided for moving the presser element to its assembled position.

The pre-assembled position of the presser element 42 thus provides several advantages. Firstly, it provides security when transporting the device. Furthermore, it guarantees reliable assembly for any type of dispenser member, in particular a pump. Pumps can have different actuation strokes. In the absence of a pre-assembled position, while the reservoir/pump unit is being assembled in the body/head unit, the pump is actuated so as to enable the actuator element 41 to become positioned below the radial flange 61 of the fastener ring 60. However, with a pump having a very small actuation stroke, there would be a risk of assembly not being achieved correctly. With the presser element 42 in its pre-assembled position when the reservoir/pump unit is assembled in the body/head unit, correct assembly is guaranteed when the presser element 42 is moved from its pre-assembled position to its assembled position. Assembling the actuator element 41 below the radial flange 61 is thus not dependent on the actuation stroke of the pump that may vary depending on the pump, but on the movement of the presser element between its pre-assembled and assembled positions, which movement is constant and predetermined. Correct assembly of the device is thus guaranteed whatever the pump used.

Although the invention is described above with reference to embodiments that group together a plurality of aspects described above, naturally those various aspects could be implemented independently of one another. Other modifications could be envisaged by the person skilled in the art, without going beyond the ambit of the present invention, as defined by the accompanying claims.

The invention claimed is:

1. A fluid dispenser device comprising:
    a body, a reservoir;
    a dispenser head incorporating a dispenser orifice; and
    a dispenser member that is mounted on said reservoir by means of a fastener ring, said dispenser member comprising a dispenser-member body and a movable member that moves axially in said dispenser-member body while said dispenser member is being actuated;
    said device further comprising a lateral actuator system that is secured to said body, said system including an actuator element that is movable, substantially transversally to the direction of movement of said movable member, between a rest position in which said dispenser member is not actuated, and an actuated position in which said dispenser member is actuated;
    said body including at least one axial guide surface for guiding said actuator element during an actuation stroke, said at least one axial guide surface being straight and stationary relative to said dispenser head and parallel to a movement axis of the movable member in the dispenser-member body while said dispenser member is being actuated;
    said actuator element including an end edge that co-operates with said at least one axial guide surface, wherein said at least one axial guide surface includes a portion having resistance means, wherein said resistance means comprises a modification to the portion of the at least one axial guide surface, the modification to the portion locally modifying friction between the end edge of the actuator element and the at least one axial guide surface, such that, in order to be passed over, said portion having resistance means requires the user to act on said lateral actuator system with an actuation force that is higher than an actuation force required without the resistance means;
    wherein all of the at least one axial guide surface is on or along the same axis; and
    wherein said end edge of said actuator element that co-operates with said at least one axial guide surface is a convex rounded surface.

2. The device according to claim 1, wherein said lateral actuator system includes a presser element that is mounted on the body to pivot about a first pivot axis, said actuator element being mounted on said presser element to pivot about a second pivot axis.

3. The device according to claim 2, wherein said actuator element includes a resilient element that co-operates with said presser element so as to urge said actuator element away from said presser element and into contact with said at least one axial guide surface.

4. The device according to claim 3, wherein the resilient element is a resilient blade.

5. The device according to claim 1, wherein said actuator element of the lateral actuator system co-operates directly with said fastener ring during actuation.

6. The device according to claim 1, wherein the dispenser member is a pump or a valve.

7. The device according to claim 1, wherein said end edge of said actuator element passes over said profile or shoulder in order to achieve actuation.

8. The device according to claim 7, wherein said profile co-operates with said actuator element at a beginning of an actuation stroke.

9. A fluid dispenser device comprising:
    a body, a reservoir;
    a dispenser head incorporating a dispenser orifice; and
    a dispenser member that is mounted on said reservoir by means of a fastener ring, said dispenser member comprising a dispenser-member body and a movable member that moves axially in said dispenser-member body while said dispenser member is being actuated;
    said device further comprising a lateral actuator system that is secured to said body, said system including an actuator element that is movable, substantially transversally to the direction of movement of said movable member, between a rest position in which said dispenser member is not actuated, and an actuated position in which said dispenser member is actuated;
    said body including at least two axial guide surfaces for guiding said actuator element during an actuation stroke, said at least two axial guide surfaces being straight and stationary relative to said dispenser head and parallel to a movement axis of the movable member in the dispenser-member body while said dispenser member is being actuated;
    said actuator element including an end edge that co-operates with said at least two axial guide surfaces;
    said device further comprising an intervening profile or shoulder between said at least two axial guide surfaces that modifies the co-operation between said end edge of said actuator element and said at least two axial guide surfaces, such that, in order to be passed over, said profile or shoulder requires the user to act on said lateral actuator system with an actuation force that is higher than an actuation force required without the profile or shoulder; and
    wherein said end edge of said actuator element that co-operates with said at least one axial guide surface is a convex rounded surface that defines a distal end shape of the actuator element.

10. A fluid dispenser device comprising:
    a body;
    a reservoir;
    a dispenser head incorporating a dispenser orifice;
    a dispenser member mounted on the reservoir by a fastener ring, the dispenser member comprises a dispenser-member body and a movable member that moves axially in the dispenser-member body while the dispenser member is actuated; and a lateral actuator system secured to the body, the lateral actuator system comprising an actuator element movable, substantially transversally to the direction of movement of the movable member, between a rest position in which the dispenser member is not actuated, and an actuated position in which the dispenser member is actuated;

the body comprises an axial guide surface that guides the actuator element during an actuation stroke in sliding movement, the axial guide surface is straight and stationary relative to the dispenser head and substantially parallel to a movement axis of the movable member in the dispenser-member body while the dispenser member is being actuated;

the actuator element comprises an end edge that co-operates with the axial guide surface;

the fluid dispenser further comprising a profile immediately followed by the axial guide surface, the profile projects away from the axial guide surface and towards the actuator element so as to engage the end edge of the actuator element, such that, in order for the profile to be passed over by the actuator element, an actuation force on said lateral actuator system is required that is higher than an actuation force that otherwise would be required without the profile; and wherein said end edge of said actuator element that co-operates with said axial guide surface is a convex rounded surface that defines a distal end shape of the actuator element.

11. The device according to claim 10, wherein the profile projects in a direction transverse to the movement axis and resists sliding movement of the end edge of the actuator element against the axial guide surface.

12. The device according to claim 10, wherein the lateral actuator system includes a presser element mounted on the body to pivot about a first pivot axis and the actuator element mounted on the presser element to pivot about a second pivot axis; and wherein the second pivot axis is disposed at a distance further away from dispenser orifice than the axial guide surface along which the end edge of the actuator element slides.

13. A fluid dispenser device comprising:
a body, a reservoir;
a dispenser head incorporating a dispenser orifice; and
a dispenser member that is mounted on said reservoir by means of a fastener ring, said dispenser member comprising a dispenser-member body and a movable member that moves axially in said dispenser-member body while said dispenser member is being actuated;
said device further comprising a lateral actuator system that is secured to said body, said system including an actuator element that is movable, substantially transversally to the direction of movement of said movable member, between a rest position in which said dispenser member is not actuated, and an actuated position in which said dispenser member is actuated;
said body including at least one axial guide surface for guiding said actuator element during an actuation stroke, said at least one axial guide surface being straight and stationary relative to said dispenser head and parallel to a movement axis of the movable member in the dispenser-member body while said dispenser member is being actuated;
said actuator element including an end edge that co-operates with said at least one axial guide surface, wherein said at least one axial guide surface includes a portion having resistance means, wherein said resistance means comprises a modification to the portion of the at least one axial guide surface, the modification to the portion locally modifying friction between the end edge of the actuator element and the at least one axial guide surface, such that, in order to be passed over, said portion having resistance means requires the user to act on said lateral actuator system with an actuation force that is higher than an actuation force required without the resistance means;
wherein all of the at least one axial guide surface is on or along the same axis; and
wherein the modification to the portion of the at least one axial guide surface is positioned to come into contact with the end edge of the actuator element after a first predetermined portion of the actuation stroke.

* * * * *